United States Patent [19]

Dai et al.

[11] Patent Number: 5,352,835
[45] Date of Patent: Oct. 4, 1994

[54] SUPPORTED CATALYSTS FOR AMINATION

[75] Inventors: Pei-Shing E. Dai, Port Arthur; Terry L. Renken, Austin; Laurence D. Neff, Port Arthur, all of Tex.

[73] Assignee: Texaco Chemical Company, White Plains, N.Y.

[21] Appl. No.: 14,583

[22] Filed: Feb. 8, 1993

[51] Int. Cl.$^5$ .................................... C07C 209/16
[52] U.S. Cl. ................................. 564/480; 502/245; 502/331; 502/337; 502/345
[58] Field of Search ............... 564/480; 502/245, 331, 502/337, 345

[56] References Cited

U.S. PATENT DOCUMENTS

| | | | |
|---|---|---|---|
| 3,637,529 | 1/1972 | Van Beek et al. | 252/459 |
| 4,524,255 | 6/1985 | Qualeatti et al. | 568/885 |
| 5,003,107 | 3/1991 | Zimmerman et al. | 564/480 |

*Primary Examiner*—Richard L. Raymond
*Assistant Examiner*—Scott C. Rand
*Attorney, Agent, or Firm*—Russell R. Stolle; Cynthia L. Kendrick

[57] ABSTRACT

Disclosed is a process for the amination of polyols to form primary amines which comprises reacting a polyoxyalkylene alcohol or polyol having a molecular weight of from about 230 to 5000 and ammonia in the presence of hydrogen over a catalyst consisting essentially of 10 to 35 wt % nickel, 1 to 20 wt % copper and 0.1 to 2.0 wt % optionally chromium or molybdenum promoter impregnated onto a $\theta$-alumina support at a temperature of 100° C. to 300° C. and a pressure of 1000 psig to 3000 psig wherein the $\theta$-alumina support results from calcining $\gamma$-alumina or pseudo-boehmite for 2-4 hours at 900°–1100° C.

11 Claims, 1 Drawing Sheet

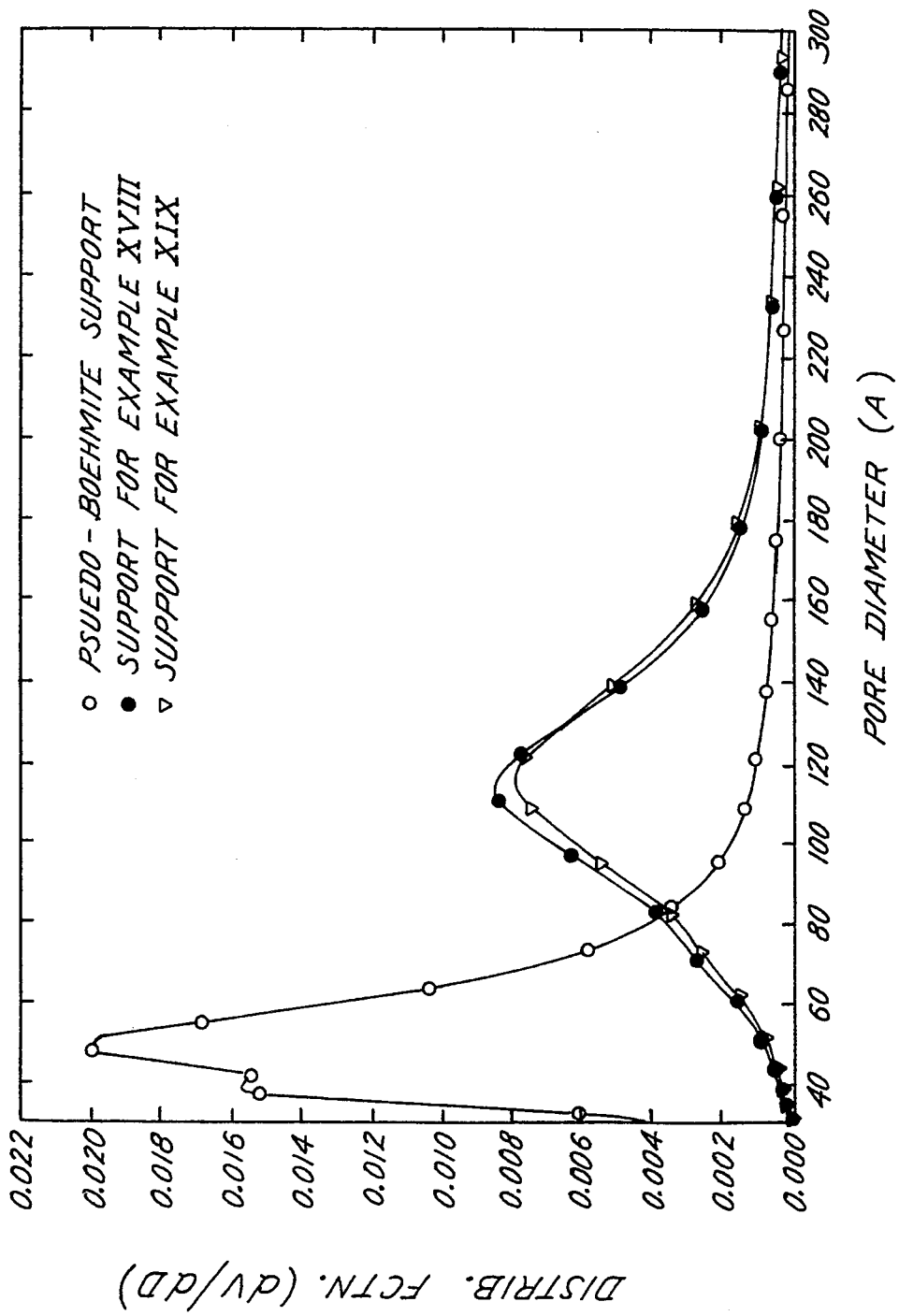

SUPPORTED CATALYSTS FOR AMINATION

CROSS-REFERENCE

This application is related to Ser. No. 08/014,590, filed of even date.

FIELD OF THE INVENTION

This invention is related to the amination of polyoxyalkylene alcohols. More particularly this invention is related to the reductive amination of polyoxyalkylene polyols made from ethylene and propylene oxides, using an improved, supported NiCu catalyst, optionally containing Mo. A significant aspect of the improvement is the use of a $\theta$-alumina support. The $\theta$-alumina supported catalyst is more active and more cost effective than currently available bulk metal catalysts and provides improvements in stability and in conversion and selectivity in the production of primary polyoxyalkyleneamines.

RELATED ART

The use of predominantly nickel and/or cobalt catalysts is known in the art for the reductive amination of polyoxyalkylene polyols to prepare the corresponding primary polyoxyalkyleneamines. In general, the catalysts have usually included Cu and one or more promoters, and have been both unsupported and supported on refractory material. Some disadvantages of using these catalysts include the formation of by-products through undesired hydrogenolysis side reactions, the formation of secondary amines and catalyst deactivation under reaction conditions.

Dobson, in European Patent Applications 356,046 and 356,047, demonstrated through examples that polyols can be aminated with ammonia at low pressure using a Raney nickel catalyst alone or in conjunction with alumina. However, this process is impractical because it leads to long reaction times and low amination levels.

EP 0,382,049 to Irgang et al. discloses the reaction of diethylene glycol (DEG) and ammonia over CoNiCu and $ZrO_2$.

EP 0,433,777 A2 to Schafer et al. discloses the reaction of polyoxyalkylene glycols and ammonia over Raney Ni and Raney Co, with powdered $Al_2O_3$.

U.S. Pat. No. 3,037,025 to Godfrey discloses the use of a NiCuCr catalyst for making dimethylpiperazine. A subsequent patent to the same assignee, describing the same catalyst was U.S. Pat. No. 3,151,115.

U.S. Pat. No. 3,151,115 to Moss et al. discloses the reaction of monoethanolamine (MEA) with ammonia over a NiCuCr catalyst.

U.S. Pat. No. 3,483,253 to Adams et al. discloses a catalyst comprising NiCuCr with polyacid to produce butylamine and 2-ethylhexylamine.

DT 27 21 033A to Jung et al. discloses the reaction of dodecanol and ammonia or dimethylamine over a Ni—Fe—Cr on $Al_2O_3$ catalyst.

EP 0,284,398A to Dobson discloses the reaction of isopropyl alcohol and ammonia over Ni—Ru—Pd-(Re,Ir) on $Al_2O_3$.

EP 0,312,253 to Kas Corporation discloses the reaction of ammonia or a primary or secondary amine over a catalyst comprising Cu(Co—Ni—Cr—Mn—Fe—Zn, etc.) and Pt.

EP 0,343,486 to Gerkin et al. discloses the reaction of an alcohol with a polyetheramine over a nickel on $SiO_2$—$Al_2O_3$ catalyst.

A NiCuCr catalyst was disclosed in U.S. Pat. No. 3,654,370 to Yeakey for the preparation of polyoxyalkylene polyamines from secondary alcohols such as propylene oxide capped polyols. This catalyst was not suitable for the amination of primary alcohols such as ethylene oxide capped polyols, because high amination levels cannot be obtained without significant degradation of the molecules due to C—O and C—C bond hydrogenolysis reactions.

U.S. Pat. No. 3,766,184 to Johansson et al. demonstrates the production of ethylenediamine (EDA) or piperazine using Fe—Ni—Co on a $Al_2O_3$ catalyst.

Boettger et al., in U.S. Pat. No. 4,014,933, disclosed that a catalyst composed of 10% Co, 10% Ni, 4% Cu and 0.4% phosphoric acid, supported on aluminum oxide or silicon oxide, could be used to aminate a polypropylene glycol with molecular weight of 1400 to 95% amination in a continuous downflow unit.

U.S. Pat. Nos. 4,111,840 and 4,123,462 disclose the use of Ni and Re or Ni, Re and B on $SiO_2/Al_2O_3$ or $Al_2O_3$ to produce EDA, piperazine and diethylenetriamine (DETA).

Habermann, in U.S. Pat. Nos. 4,152,353 and 4,153,581, disclosed that catalysts composed of approximately 30% Ni (or 30% Co), 63% Cu and 7% of either Fe, Zn or combinations thereof can be used to aminate low and high molecular weight alcohols, such as PPG-400, a propylene glycol with molecular weight of 400.

In U.S. Pat. No. 4,209,424 (June 1980), LeGoff et al. discloses an amination catalyst comprising at least one active metal from the group of transition metals consisting of nickel, cobalt and copper, uniformly combined with a refractory microporous substrate having a specific surface between 10 and 300 $m^2/g$ and a pore diameter less than 5000 Å, wherein the transition metal represents 30-70% of the total catalyst weight.

U.S. Pat. No. 4,618,717 to Texaco discloses an unsupported NiCuCr catalyst for producing 2-(2-methoxy)ethylamine.

Cu and Ni are supported on $Al_2O_3$ and $CeO_2$ for use in the production of ethylamine, diethylamine and triethylamine in U.S. Pat. No. 4,760,190.

Larkin and Renken disclosed in U.S. Pat. No. 4,766,245 that Raney nickel catalyst in granular form was highly active and gave high selectivity to primary amine in the amination of hydroxyterminated polyoxyalkylene compounds, provided the polyols have a molecular weight of 500 or greater. Raney nickel suffers from the disadvantage that it deactivates in the presence of water. Water, of course, is produced in the amination reaction. The rate of deactivation is proportional to the amount of water formed in the reaction. Hence, low molecular weight polyols produce a greater amount of water in the reaction and, therefore, deactivate Raney nickel faster than high molecular weight polyols. Another disadvantage of Raney nickel is that it deactivates on exposure to oxygen. Thus, catalyst storage can be a serious problem.

In U.S. Pat. No. 4,855,505, NiCu and Ru are deposited on alumina for use in the amination of monoethanolamine (MEA), diethanolamine (DEA), aminoethylethanolamine (AEEA) and ethylene glycol (EG).

A U.S. Pat. No. 4,912,260 to Dobson et al. (March 1990) discloses a process for the production of an amine by reacting, for example, an alcohol and ammonia in the presence of a catalyst comprising nickel, ruthenium and at least one other transition metal which can be on a γ-alumina support.

In U.S. Pat. No. 4,960,942 to Gerkin et al. there is disclosed a nickel on silica alumina catalyst for use in producing N-alkyl JEFFAMINE ® amine products.

Schoenleben and Mueller, in U.S. Pat. No. 4,973,761, disclosed a process for the reductive amination of polyoxytetramethylene glycols. By example, polyols with molecular weights of 640 and 4000 were aminated using a NiCoCu on alumina catalyst. The products were high in secondary amine due to the relatively unhindered primary hydroxyl groups on the starting polyols.

Zimmerman and Larkin disclosed in U.S. Pat. No. 5,003,107 the preparation of polyoxytetramethylene diamines by reductive amination of the corresponding polyoxytetramethylene glycol, made by polymerizing tetrahydrofuran, using a catalyst with composition of 70–75% Ni, 20–25% Cu, 0.5–5% Cr and 1–5% Mo on an alumina support-free basis. Amination levels above 90% with selectivities to primary amine of greater that 90% were demonstrated by amination of a 1000 molecular weight polyoxytetramethylene glycol.

Many of the catalysts discussed above are expensive to prepare. Most of the amination catalysts described in the art are very limited in their usefulness. Few provide high conversion to amines from a broad range of alcohols. Many are only suitable for the amination of higher molecular weight polyoxyalkylene polyols. Others are not suitable for the amination of primary alcohols.

Some amination catalysts are quickly deactivated by the formation of significant amounts of water formed in the production of low molecular weight products. Other common problems include the formation of byproducts through undesirable hydrogenolysis side reactions, as well as the formation of secondary amines.

With certain catalysts, the conversion and selectivity leave much to be desired. Finally, some of these catalysts are quite expensive, exhibit the disadvantages defined above and are not stable for long periods of time.

It would be a significant advance in the art if an amination catalyst were available which was more stable for longer periods of time in the presence of water and which gave higher selectivity to primary amines.

SUMMARY OF THE INVENTION

In accordance with the foregoing it is an objective of this invention to develop a cost-effective amination catalyst which affords good physical stability and high productivity and selectivity to primary amines in the amination of polyols prepared from ethylene oxide and propylene oxide. To that end the present invention provides an improved catalyst and a process for preparing polyoxyalkylene primary amines from the corresponding polyols containing oxyethylene and oxypropylene groups. The catalyst is useful for polyols having molecular weights of 230 to about 5000.

Alumina with a large mesopore diameter (100–200 Å) and high macroporosity (PV>500 Å: 0.10–0.30 cc/g) is the most preferred support for the amination catalysts.

DRAWINGS

FIG. 1 is a graph representing pore distributions for alumina supports.

DETAILED DESCRIPTION OF THE INVENTION

This invention describes a process for selective preparation of primary polyoxyalkyleneamines. According to the invention an alcohol, glycol or polyol reaction product is reacted with ammonia in the presence of hydrogen and a catalyst consisting essentially of nickel and copper and optionally, molybdenum impregnated on at least 50 wt % of the total weight of the catalyst of a refractory metal oxide support which is preferably alumina, and particularly θ-alumina.

As stated the reactants useful in the invention are alcohols. The alcohol may be monohydric, but can be a glycol, and in the instant invention is usually a polyoxyalkylene polyol. A variety of polyols are useful as reactants in the instant invention. One group of polyols which are particularly suitable have the formula:

$$\begin{array}{cc} CH_3 & CH_3 \\ | & | \\ HOCHCH_2O(CH_2CHO)_n\!-\!H \end{array}$$

where n=2–100, and the polyols have a molecular weight from about 230 to 5000. Commercial products of this description include JEFFOX ® polypropylene glycols(PPG). Generally the viscosity of these polyols increases with increasing molecular weight and the solubility decreases with increasing molecular weight. For JEFFOX ® PPG-230, 400, 2000 and 5000 n=2.5, 5.6, 33.1, and 84.7 respectively.

Also demonstrated is the amination of Thanol ® G-5000. Thanol ® G-5000 is the tradename for a polyol manufactured by Texaco Chemical Company having three hydroxyl groups per molecule and an average molecular weight of about 5000.

Other reactants which may be used include alkoxylates made from combinations of ethylene and propylene oxides. Such materials can be made by first ethoxylating an alcohol or glycol with ethylene oxide and then "capping" by reaction with propylene oxide. Some of these materials that have been aminated are currently being sold by Texaco Chemical Company as JEFFAMINE ® ED and SURFONAMINE ® series amine products.

Other reactants which may be used include reaction products of ethylene oxide and nonylphenol. These products are available commercially as SURFONIC ® Surface Active Agents produced by Texaco Chemical Co. Particularly useful is the "N" series represented by:

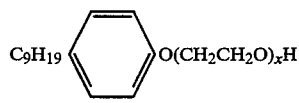

where x=1–20 and the products are designated by a number following the letter "N" and the number represents a tenfold multiple of the molar ratio of ethylene oxide in the adduct. In addition, these materials can be "capped" by reaction with propylene oxide and the resultant polyol can be aminated.

The catalyst consists essentially of nickel, copper and, optionally, other promoters including chromium, iron, manganese, molybdenum or zinc deposited on an oxide support. The support comprises at least 50 wt % of the catalyst. Many of the catalysts described in the art contain considerably lower weight percent of the support material. The preferred oxide support is alumina. The alumina is most preferred in the γ or θ form and substantial improvements are documented using θ-alumina.

The activity and selectivity of the θ-alumina supported Ni and Cu catalyst of this invention are higher than observed using Raney nickel (i.e. U.S. Pat. No. 4,766,248). Further the catalyst is less susceptible to deactivation than Raney nickel. The catalyst of this invention is capable of at least two-fold higher productivities than the NiCuCr bulk metal catalyst described in U.S. Pat. No. 3,654,370 as demonstrated in instant Examples I, VI, IX, X and XIV. This catalyst is also substantially less expensive than other catalysts of this type used in the art.

The quantity of nickel, copper and molybdenum compounds which are employed in the catalyst may vary. Good results are observed where the catalyst consists essentially of 10–40 wt % nickel, 2–25 wt % copper and 0.1 to 2 wt % molybdenum as well as at least 50 wt % of the refractory metal oxide support. A preferred catalyst composition comprises 15 to 30 wt % nickel and 3–20 wt % copper and 0.5 to 1.0 wt % of molybdenum. The catalyst can be produced by repetitive deposition of Ni and Cu carbonate or Ni and Cu nitrate in combination with ammonium molybdate.

The use of a catalyst support material such as alumina allows for the total metal loading of the active metals to be reduced significantly and still provide substantial improvements in conversion and selectivity, thus demonstrating a more efficient, less expensive catalyst which provides improved results. The total active metal loading was lowered to 20 to 40 wt % while maintaining effective proportions of the respective metals. The active metals are essentially dispersed uniformly throughout the support and over the support surface to enhance catalyst activity and improve synthesis of primary polyoxyalkyleneamines. From the examples, it is noted that improvement in amination activity seemed to level off near a total metal loading of about 30 wt %.

The catalyst effectiveness is apparently influenced by both the physical and chemical properties of the catalyst. Physical properties such as aspect ratio (pellet diameter and length), packed density, surface area and total pore volume have been identified which assist in achieving optimum catalyst activity. The intrinsic activity is mainly controlled by the chemical properties such as bulk metal composition, active metal phases, metal dispersion and morphology, impregnation profile and metal particle size distribution. External mass transport and intrapore diffusion could play an important role in the synthesis of polyoxyalkyleneamines.

As discussed above, the catalyst can be greatly improved by using a large mesopore diameter alumina support. Alumina supports having the pore volumes and pore diameters indicated as useful can be technologically difficult to manufacture, however the alumina can be deposited on silica. Silica beads and silica extrudates offer high total pore volume and large pore diameters, along with strong mechanical strength and are much less expensive.

The supports in the instant invention comprised either γ-aluminas stabilized with 2.0 wt % silica, large pore silica beads or extrudates coated with activated alumina or θ-alumina. The alumina supports used in these studies, both from Haldor-Topsoe and American Cyanamid, were in the form of 1/32" extrudates. Table A specifies the physical properties of γ-alumina supports employed in Examples I→XVI.

The θ-alumina support is produced by calcination of a γ-alumina support for 1 to 4 hours at a temperature from about 800° to 1200° C., thereby increasing pore size. A preferred temperature is about 1050° C. Thereafter the θ-alumina support is impregnated with metal salt solution. The use of θ-alumina is demonstrated in Examples XVII to XXII.

Suitable θ-aluminas are those which satisfy the following X-ray diffraction pattern.

| d(10$^{-10}$m) | I/Io |
| --- | --- |
| 1.39 | 100 |
| 2.85 | 75–85 |
| 2.72 | 60–80 |
| 2.43 | 70 |
| 2.01 | 45–80 | having a surface area between 50 and 200 m$^2$/g and being substantially free of pores with a diameter less than 4.0 nm. The catalyst has a pore size distribution substantially between 3.5 and 30 nm, rather than between 3.5 and 120 nm as measured by nitrogen desorption. (see FIG. 1)

TABLE A

| | Physical Properties of Alumina Supports | | | |
| --- | --- | --- | --- | --- |
| Catalyst Support Type | TK-753 Alumina | SN-6493 Alumina/ 2% Silica | SN-6651 Alumina/ 2% Silica | SN-6790 Alumina |
| TPV, cc/g | 0.93 | 0.80 | 0.99 | 0.92 |
| PV >250A cc/g | 0.31 | 0.05 | 0.27 | 0.15 |
| PV >160A cc/g | 0.44 | 0.09 | 0.32 | 0.19 |
| PV <160A cc/g | 0.49 | 0.71 | 0.67 | 0.73 |
| PV <100A cc/g | 0.09 | 0.31 | 0.34 | 0.65 |
| PV 100-160A cc/g | 0.40 | 0.40 | 0.33 | 0.08 |
| (% of TPV) | (43) | (50) | (33) | (9) |
| PM at (dv/dD) max Å | 120 | 100 | 97 | 87 |
| PM (BET), Å | 94 | 109 | 107 | 73 |
| Surf. Area, m$^2$/g | 192 | 223 | 215 | 308 |

The pore mode is based on nitrogen BET analysis using the desorption isotherm and consideration only of pore diameters <600Å.

The temperature range of the amination reaction which can usefully be employed is a variable depending upon other experimental factors, including the pressure, contact time of reactants with catalyst, and choice of particular catalyst. The range of operability is from about 100° C. to 300° C. A narrower range of 180° C. to 240° C. is preferred and reflects the range providing the best selectivity for primary amine and yield of primary amine.

Pressures of 1000 psig to 3000 psig can be used. The preferred range is 1500 psig to 2500 psig.

The catalysts of the instant invention were tested for their activities in the amination of polyols, such as, for example PPG-2000, G-5000 and PPG-230. The test was conducted charging 75 cc or 100 cc of catalyst in a 100 cc up-flow fixed bed reactor. The reactor tube was about 30 inches in length and about 0.5 inch in diameter. The catalyst was activated by reducing in hydrogen at 325° C. overnight prior to contacting the liquid feed.

Polyol and ammonia were fed to the reactor using separate pumps. In the reactor configuration, for some of the experiments, a static mixer was added upstream to the reactor to improve the mixing of polyol, ammonia and hydrogen. The hydrogen was metered using a mass flow controller. The liquid polyol and ammonia feeds were delivered by separate pumps. The hydrogen rate was adjusted to maintain 2.0 SCF/lb (SCF=standard cubic feet) of polyol fed to the reactor. Average liquid feed rates were calculated from data just before and during the taking of samples. The reactor pressure was maintained at approximately 2000 psig in all experiments. The temperature was varied from about 190° C. to 230° C.

Total acetylatables, total amine, primary amine and water contents were determined on samples that were stripped free of ammonia, water and light ends. The conversion of alcohol to amine can be calculated as:

$$\frac{\text{Total amine}}{\text{Total Acetylatable}} \times 100\%$$

and selectivity to primary amine can be defined as:

$$\frac{\text{Primary Amine}}{\text{Total Amine}} \times 100\%$$

However, for the purposes of comparison, the levels of total and secondary amine reflect catalyst performance, and are used here.

The typical data that represent the amination activities of the supported catalysts of this invention using PPG-2000 and G-5000 polyols are given in Tables III-VII.

Typically, various primary amines are generated continuously in up to ca. 98 wt % concentration in the liquid product at total liquid hourly space velocities (LHSV) of at least 0.4 to 1.5g alcohol/hr-cc and relatively mild reactor temperatures.

$$LHSV = \frac{\text{Grams of Liquid Feed Run Through the Reactor Per Hour}}{\text{Volume of Catalyst in Reactor}}$$

The examples which follow illustrate the synthesis of primary amines from polyols and ammonia using improved NiCu catalysts on $\gamma$ or $\theta$-alumina supports. Examples XVII through XXII demonstrate the preferred catalyst on a $\theta$-alumina support.

The examples are only intended as a means of illustration and it is understood the invention is not meant to be limited thereby.

EXAMPLE I

A 500 cc sample of bimodal $\gamma$-alumina support labeled as TK-753 and manufactured by HALDOR-TOPSOE company in the form of 1/32" extrudes was dried at 120° C. overnight. An impregnating solution of Ni and Cu was prepared by heating nickel nitrate hexahydrate (292 g) and copper nitrate hemipentahydrate (190.3 g) at 140° C. in a 1-liter flask. The "melt" was diluted with deionized water to a total volume of 300 cc. This impregnating solution was added dropwise to 500 cc of the dried alumina support. The wet impregnated support was then dried at 120° C. overnight. The impregnation procedures were repeated using another aliquot of 300 cc of the impregnating solution. The resulting support was dried at 120° C. overnight and calcined at 426° C. for 4 hours and 676° C. for 4 hours.

EXAMPLES II–VI

For catalysts of Example II to VI the Ni and Cu contents were varied while holding the total metal loading at about 30 wt %. For each of the catalysts the TK-753 alumina support was impregnated with aqueous Ni and Cu nitrate solutions, followed by drying and calcination steps similar to those described in Example I. Data for these catalysts are shown in Table I.

EXAMPLES VII–VIII

A hydrotreating catalyst for Haldor-Topsoe that contained 13.1 wt % $MoO_3$, 3.5 wt % NiO and 4.1 wt % $P_2O_5$ on TK-753 alumina, was used in the preparation of catalyst Examples VII and VIII. The catalysts were made by using the double impregnation procedures with aqueous nickel and copper nitrate solutions as described in Example I. Composition data are given in Table II.

EXAMPLES IX–XV

Three $\gamma$-alumina supports, as 1/32" extrudates, with varied pore structures obtained from American Cyanamid (ACY) with respective code numbers SN-6493, SN-6790 and SN-6651 were used for the preparation of catalyst Examples IX–XV. The catalysts of Examples IX and X, made by following the preparation procedures in Example I, were designated Examples XI and XII and were prepared by impregnating the desired amounts of metals onto the supports in a single step. Example XIII was prepared by doubly impregnating SN-6651 support with a solution which contained 55.5 g of nickel nitrate and 42.8g of copper nitrate each time. Example XIV was prepared using similar methods except that 30.6 g of SN-6651 alumina support, 50.2 g of nickel nitrate and 40 g of copper nitrate were employed. The rest of procedures were identical to those used in Example I. Example XV was the Co—Cu counterpart of Example XIII. The metal contents of the metal oxide catalyst precursors are presented in Table II.

For comparison, a NiCuCr bulk metal catalyst described in U.S. Pat. No. 3,634,370 in the form of $\frac{1}{8}$" diameter $\times \frac{1}{8}$" length pellets prepared by Engelhard was also tested in PPG-2000 and G-5000 aminations. Strictly speaking, comparison of the performances of this catalyst with the supported catalysts are complicated by the fact that the extrudate offers 2.4 times the available geometric surface area of the larger $\frac{1}{8}"\times\frac{1}{8}"$ tablet. In addition, the surface areas, pore volumes, metal crystallite sizes are all likely to be different for the two types of catalysts. All of these factors contribute to catalyst performance. In general, supported catalysts allow for greater control of catalyst properties that affect performance and are usually less expensive than bulk metal catalysts. It is impractical if not impossible to make catalyst pellets as small as 1/32" diameter, while it is routine to make extrudates this size. With this in mind, it is instructive to compare the results obtained for supported catalysts with the bulk metal catalysts, to demonstrate the superior performance obtainable with the supported catalyst.

EXAMPLE XVI

A NiCuMo catalyst on alumina support SN-6913 was made by ACY using a method which comprised comulling the nickel nitrate, copper nitrate and molybdenum trioxide with alumina gel followed by extrusion and calcination at about 600° C. The resulting catalyst contained 17.8 wt % Ni, 16.6 wt % Cu and 0.9 wt % Mo.

TABLE I

Metal Compositions for Catalyst Preparations of NiO/CuO on TK-753 Alumina

| Example | Ni wt % | Cu Wt % |
|---|---|---|
| I | 20.9 | 17.3 |
| II | 6.1 | 25.0 |
| III | 27.2 | 0.1 |
| IV | 0.1 | 29.8 |
| V | 9.3 | 19.4 |
| VI | 21.2 | 7.1 |

Note:
Metal analysis on calcined catalysts by ICP analysis.

TABLE

Selected Physical Characteristics of Example Catalysts

| Example | Surface Area ($m^2/g$) | Total Pore Volume (cc/g) | Pore Volume >250Å (cc/g) | Pore Volume >100Å (cc/g) | Pore Mode (Å) |
|---|---|---|---|---|---|
| I | 87 | 0.45 | 0.13 | 0.42 | 117 |
| II | 98 | 0.50 | 0.15 | 0.45 | 110 |
| III | 120 | 0.56 | 0.18 | 0.40 | 95 |
| IV | 114 | 0.56 | 0.16 | 0.49 | 107 |
| V | 114 | — | — | — | 93 |
| VII | 89 | 0.53 | 0.25 | 0.53 | 118 |
| VIII | 88 | 0.52 | 0.25 | 0.51 | 141 |
| XII | 108 | 0.45 | 0.13 | 0.36 | 94 |
| XIII | 139 | 0.58 | 0.16 | 0.47 | 100 |
| XV | 124 | 0.67 | 0.19 | 0.54 | 121 |
| XVI | 135 | 0.59 | 0.19 | 0.42 | 84 |
| XVIII | 133 | 0.56 | 0.18 | 0.46 | 100 |
| XIX | 112 | 0.49 | 0.17 | 0.42 | 94 |
| XX | 121 | 0.52 | 0.18 | 0.41 | 93 |
| XXI | 73 | 0.46 | 0.21 | 0.45 | 125 |
| XXII | 103 | 0.41 | 0.14 | 0.28 | 82 |

TABLE II

Metal Compositions for Catalyst Preparations of NiO/CuO on Alumina Extrudate Supports

| Example | Support | Mo Wt % | Ni wt % | Cu Wt % |
|---|---|---|---|---|
| VII | TK-753 | 7.9 | 15.5 | 14.9 |
| VIII | TK-753 | 8.2 | 5.7 | 23.6 |
| XI | SN-6493 | 0 | 13.9 | 13.6 |
| X | SN-6790 | 0 | 13.7 | 13.5 |
| XI | SN-6493 | 0 | 13.0 | 14.9 |
| XII | SN-6651 | 0 | 17.6 | 17.9 |
| XIII | SN-6651 | 0 | 13.9 | 13.6 |
| XIV | SN-6651 | 0 | 16.7 | 16.7 |
| XII | SN-6651 | 0 | Co 13.7 | 13.9 |

Note:
Metals analysis on calcined catalysts by ICP.

Table III illustrates the performances of NiCu catalysts on a TK-753 alumina support for the amination of PPG-2000.

For the supported catalysts of Table III, it appears that amination activity is proportional to the nickel content. However, some minimum amount of copper is necessary to properly activate the catalyst, as evidenced by the lower activity of Example III, a 25.5% Ni, 0% Cu catalyst. The 28% Cu, 0% Ni catalyst of Example IV gave only low amination. Examples I and VI, which have the highest Ni content of the Cu containing supported catalysts, also exhibited the highest activity. The supported catalysts, especially Examples I and VI, gave much higher amination than the bulk metal NiCuCr catalyst of U.S. Pat. No. 3,654,370.

Note also that the catalyst of Example VII which contained about 7.9 wt % Mo and 15 wt % each of Ni and Cu gave the lowest activity. It is apparent that high loading of Mo had an adverse effect on the amination activity.

The selectivities to primary amine obtained using all the catalysts of Table III were found to be high, as exemplified by the low secondary amine levels. The percent (%) selectivity is most important at high amination levels, where the supported catalysts of Examples I, II, III, V and VI afforded less secondary amine than the bulk metal NiCuCr catalyst.

The catalysts of Examples I and VI were also tested in G-5000 amination. Run conditions and results of this work are given in Table IV. The catalysts gave the same relative performances here as in PPG-2000 amination as discussed above.

TABLE III

Activities of NiCu Catalysts Supported on TK-753 Alumina in PPG-2000 Amination

| | 200° C. | | 230° C. | | | | |
|---|---|---|---|---|---|---|---|
| Example | Total Amine meq/g | Secondary Amine meq/g | Total Amine meq/g | Secondary Amine meq/g | % Ni | % Cu | % Other |
| I | 0.843 | .004 | .977 | .003 | 20.7 | 17.5 | — |
| II | .536 | .007 | .946 | .008 | 7.1 | 25.7 | — |
| Bulk NiCuCr | .438 | .007 | .815 | .017 | 72 | 12 | 2 Cr |

RESULTS OBTAINED USING REACTOR WITH FEED MIXER

| III | .468 | .005 | .951 | .010 | 25.5 | 5.0 | — |
| IV | .090 | .008 | .082 | .011 | 0 | 27.8 | — |
| V | .638 | .007 | .961 | .009 | 9.7 | 18.7 | — |
| VI | .882 | .006 | .971 | .009 | 20.5 | 7.1 | — |
| VII | .012 | .003 | .055 | .003 | 15.5 | 14.9 | 7.9 Mo |

Note:
All samples were taken at a polyol LHSV of 1.0. 75 cc of catalyst was charged to the reactor for Examples I, II and for the bulk metal catalyst. 100 cc of catalyst was charged for Examples III to VII. Polyol and ammonia feed rates were each held at 75 g/hr and the hyrdrogen at 10.3 l/hr for the runs with 75 cc of catalyst. The polyol and ammonia rates were each 100 g/hr and the hydrogen rate 12.4 l/hr for the runs with 100 cc catalyst charge. The pressure was held constant at 2000 psig. Samples were taken at temperatures of 200 to 230° C.
The total amine and secondary amine values were determined by potentiometric titration and are given in units of meq/g (meq amine per gram of sample). The maximum total amine content for aminated PPG-2000 is about 1.0 meq/g.

TABLE IV

Activities of NiCu Catalysts Supported on TK-753 Alumina in G-5000 Amination

| | 200° C. | | 230° C. | |
|---|---|---|---|---|
| Example | Total Amine meq/g | Secondary Amine meq/g | Total Amine meq/g | Secondary Amine meq/g |
| I | .434 | .005 | .574 | .002 |
| II | .225 | .003 | .478 | .003 |
| NiCuCr | .133 | .007 | .288 | .011 |

RESULTS OBTAINED USING REACTOR WITH FEED MIX

| III | .287 | .005 | .547 | .003 |
| IV | .009 | .006 | .042 | .002 |
| V | .297 | .004 | .551 | .002 |
| VI | .497 | .007 | .590 | .001 |

Note:
The same catalyst charges were used in these experiments as those described in Table III. Polyol and ammonia feed rates were each held at 75 g/hr for all the runs. The hydrogen rate was held constant at 9.4 l/hr the run of Examples I-VI and 10.3 l/hr for the control run. The pressure was held constant at 2000 psig. Samples were taken at temperatures of 200° to 230° C.
The total amine and secondary amine values were determined by potentiometric titration and are given in units of meq/g (meq amine per gram of sample). The maximum total amine content for aminated G-5000 is about 0.60 meq/g.

The NiCu and CoCu catalysts of Examples IX to XV, prepared from 1/32 inch American Cyanamid γ-alumina supports, were tested in PPG-2000 and G-5000 aminations. Also tested were the catalyst of Example XVI made by American Cyanamid, the ⅛×⅛ inch bulk metal NiCuCr catalyst, a 47.5% nickel on alumina catalyst (D-4132) from Engelhard, and a 38.4% Ni, 5.9% Cr, 1.1% Cr and 0.6% Mo on alumina catalyst (Ni-2728) from Engelhard. The latter two catalysts were not made by the metal salt impregnation technique, but rather by extrusion (to ca. 1/32 inch) of a slurry of metal oxides and alumina, followed by drying, calcination and activation with hydrogen. Run conditions and results are summarized in Tables V and VI.

Results for catalysts of Examples IX, X and XIII are of particular interest. These catalysts all have identical metal contents but were made from three different γ-alumina support materials. The catalyst made from support SN-6651 was the most active, followed by SN-6790, then SN-6493. The porosity data in Table A shows that SN-6651 has the largest macroporosity (e.g. pore volume >250 Å, 0.32 cc/g), followed by SN-6790 (0.15 cc/g, then SN-6493, 0.05 cc/g). Thus, it appears that supports with high mesopore modes and high macroporosity afford catalysts with higher polyol amination activity.

The catalysts made from SN-6651 were comparable in activity to the Engelhard D-4132 catalyst that contained 47.5% Ni and more active than Ni-2728 catalyst that contained 38.4% Ni. The higher activity with lower nickel content is attributable to the accessibility of the nickel.

The catalyst of Example XVI made by co-extrusion of metal salts with alumina gels unexpectedly gave the lowest conversion in PPG-2000 amination. This may have been due to incomplete or improper activation of the catalyst.

TABLE V

Activities of NiCu Catalysts on ACY Supports in PPG-2000 Amination

| | | 200° C. | | 230° C. | | | | |
|---|---|---|---|---|---|---|---|---|
| Example | Support | Total Amine | Secondary Amine | Total Amine | Secondary Amine | % Ni | % Cu | Other |
| XII | SN-6651 | .941 | .008 | .980 | .009 | 17.6 | 17.9 | — |
| XIV | SN-6651 | .979 | .011 | 1.016 | .015 | 16.7 | 16.7 | — |
| XV | SN-6651 | .952 | .006 | .986 | .011 | — | 13.9 | 13.7 Co |
| XVI | SN-6913 | .179 | .006 | .617 | .008 | 18.7 | 18.2 | 1.0 Mo |
| D-4132 | (Engelhard) | .952 | .005 | .959 | .014 | 47.5 | — | — |
| NiCuCr | None | .438 | .007 | .815 | .017 | 72 | 12 | 1 Cr |
| Ni-2728 | (Englehard) | .856 | .004 | .986 | .008 | 38.4 | 5.9 | 1.1 Cr 0.6 Mo |
| IX | SN-6493 | .687 | .006 | .969 | .005 | 13.9 | 13.6 | — |
| X | SN-6790 | .730 | .004 | .968 | .008 | 13.7 | 13.5 | — |
| XIII | SN-6651 | .910 | .008 | .977 | .004 | 13.9 | 13.6 | — |

Note:
All samples were taken at a polyol LHSV of 1.0. 75 cc of catalyst was charged to the reactor for Examples XII, XVI, D-4132 and for the bulk metal catalyst. 100 cc of catalyst was charged for Examples XV, IX, X, XIII and Ni-2728. 55 cc of catalyst was charged for Example XIV. Polyol and ammonia feed rates were the same for each run, adjusted to maintain a LHSV of 1.0 g/hr/cc catalyst volume. The hydrogen rate was adjusted to about 2.0 SCF/lb polyol feed for each run. The pressure was held constant at 2000 psig. Samples were taken at temperatures of 200° to 230° C.
The total amine and secondary amine values were determined by potentiometric titration and are given in units of meq/g (meq amine per gram of sample). The maximum total amine content for aminated PPG-2000 is about 1.0 meq/g.

TABLE VI

Activities of Supported NiCu Catalyst in G-5000 Amination

| | | 200° C. | | 230° C. | |
|---|---|---|---|---|---|
| Example | LHSV G/HR-CC | Total Amine | Secondary Amine | Total Amine | Secondary Amine |
| XII | 1.0 | .489 | .007 | .591 | .006 |
| XIV | 1.0 | .468 | .011 | .593 | .009 |
| XV | 1.0 | .513 | .002 | .576 | .007 |
| D-4132 | 1.0 | .487 | .008 | .579 | .009 |
| NiCuCr | 1.0 | .133 | .007 | .288 | .011 |
| Ni-2728 | 1.0 | .440 | .008 | .577 | .009 |
| IX | 0.75 | .360 | .005 | .568 | .008 |
| X | 0.74 | .330 | .006 | .554 | .008 |
| XIII | 0.81 | .505 | .004 | .591 | .006 |

Note:
The same catalyst charges were used in these experiments as those described in Table V. Polyol and ammonia feed rates were each held at 75 g/hr for all the runs, except for Example XIV, where the rates were 55 g/hr. The hydrogen rate was adjusted to about 2.0 SCF/lb polyol feed to the reactor. The pressure was held constant at 2000 psig. Samples were taken at temperatures of 200° to 230° C.
The total amine and secondary amine values were determined by potentiometric titration and are given in units of meq/g (meq amine per gram of sample). The maximum total amine content for aminated G-5000 is about 0.60 meq/g.

EXAMPLES XVII–XXII

The catalysts of Examples XVII to XXII were prepared using both gamma (Examples XVII, XX and XXII) and Θ-alumina extrudates (Examples XVIII, XIX and XXI) from two different alumina sources (SN-7063 and TK-753). In general, the Θ-alumina substrates were prepared by calcining the precursor alumina according to the following schedule of steps: room temperature to 538° C., 538° C. to 815° C., 815° C. to 1050° C. and hold at 1050° C. for 4 hours.

The resulting support was impregnated using the following procedures:

(1) 123.5 g of nickel nitrate hexahydrate and 13.6 g of copper nitrate hemipentahydrate were melted and the melt was diluted with distilled water to a final volume of 80 cc.

(2) 126 g of alumina was impregnated with 80 ml of aqueous metal nitrate solution by mixing at room temperature.

(3) The support was oven dried at 121° C. for 2 hours and calcined at 315° C. for 4 hours.

(4) 128.5 g of nickel nitrate and 13.6 g of copper nitrate were melted and the melt was diluted with water to a final volume of 75 cc.

(5) The support was impregnated with 75 cc metal nitrate solution at room temperature.

(6) The support was dried at 121° C. for 2 hours and calcined at 482° C. for 8 hours.

The metal content, pore structures and surface area were measured on the supported metal oxide catalyst precursors. The catalysts were activated by reduction with hydrogen in the reactor (325° C., overnight) prior to testing in PPG-2000 amination.

The amination runs were conducted using 100 cc of catalyst in an upflow tubular reactor. The total amine values shown were determined for samples taken at polyol and ammonia feed rates of 140 g/hr, a hydrogen feed rate of 17.5 1/hr, 200 psig and 200° C. The results of amination experiments are given in Table VII.

The catalysts of Examples XVII-XXII each contain about 20% Ni and 7.5% Cu. Examples XVII-XIX involve catalysts prepared from SN-7063 alumina extrudates. Thermal treatment of the support prior to catalyst preparation greatly improved the activity of the catalyst, as demonstrated by the amine content of amination products. Likewise, catalysts made from thermally treated TK-753 (Example XXI) gave higher amination than untreated TK-753 (Example XX). The catalyst of Example XXII was prepared from untreated TK-753, but contained a higher Ni content. The higher Ni content increased the activity of this catalyst over that of Example XX, but it was still less active than the catalyst of Example XXI.

Thermal treatment of the support materials caused the phase of the alumina to change (from boehmite for SN-7063 and from gamma for TK-753) to the theta phase. Accompanying these phase changes were decreases in surface areas and increases in pore mode (diameter). The larger pores of the theta supports are likely responsible for the increased activities of the catalysts.

TABLE VII

| Expl No. | Wt % Ni | Wt % Cu | Support | PM A | TPV cc/g | SA m2/g | TotAM meq/g |
|---|---|---|---|---|---|---|---|
| XVII | 18.8 | 7.0 | SN-7063, Untreated Gamma Al$_2$O$_3$ | <49 | 0.57 | | 0.260 |
| XVIII | 19.8 | 7.3 | SN-7063, Calcined @ 950° C. for 4 hrs., Theta Al$_2$O$_3$ | 100 | 0.56 | 133 | 0.627 |
| XIX | 19.9 | 7.6 | SN-7063, Calcined @ 1050° C. for 4 hrs., Theta Al$_2$O$_3$ | 94 | 0.49 | 112 | 0.884 |
| XX | 19.9 | 7.6 | TK-753, Untreated Gamma Al$_2$O$_3$ | 83 | 0.52 | 121 | 0.657 |
| XXI | 18.9 | 18.9 | TK-753, Calcined @ 1050° C. for 2 hrs., Theta Al$_2$O$_3$ | 125 | 0.46 | 73 | 0.845 |
| XXII | 27.5 | 7.6 | TK-753, Untreated Gamma Al$_2$O$_3$ | 82 | 0.41 | 103 | 0.789 |

PM = Micropore Mode (dV/dr maximum in BET desorption)
TPV = Total Pore Volume in Hg Porosimetry
SA = Surface Area
Amination Condition: 100 cc Catalyst; 140 g/hr PPG-2000; 140 g/hr NH$_3$; 17.51/hr H$_2$; 200° C.; 2000 psig

What is claimed is:

1. In a process for the amination of alcohols to form primary amines which comprises reacting a polyoxyalkylene alcohol or polyol having a molecular weight of from 230 to 5000 with ammonia in the presence of hydrogen, the improvement comprising reacting said alcohol or polyol with ammonia over a catalyst composition consisting essentially of:

15–30 wt % nickel and 3–20 wt % copper and optionally 0.5–1 wt % molybdenum on a support consisting essentially of γ-alumina characterized by a total pore volume by mercury intrusion of about 0.70 to 1.2 cc/g and a pore mode (diameter) between 70 and 110 Å as measured by nitrogen desorption wherein the total active metal loading is 10–40 wt % of the catalyst as metal and at least 50 wt % of the total catalyst is γ-alumina support.

2. The process of claim 1 wherein the γ-alumina support is characterized by having a pore volume distribution such that pores having diameters of less than 100 Å constitute about 30% to 50%, pores having diameters of 100–160 Å constitute about 30% to 50%, pores having diameters greater than 160 Å constitute about 5% to 35%, and pores having diameters greater than 250 Å constitute about 5% to 35% of the total pore volume of said catalyst support measured by mercury porosimetry.

3. The process of claim 1 wherein the ratio of polyol to ammonia reactants is from 1:3 to 3:1 wt/wt and the amount of hydrogen reactant is 0.5 to 3.0 SCF/lb of polyol.

4. The process of claim 1 wherein the temperature is 180° C. to 240° C.

5. The process of claim 1 wherein the pressure is 1500 psig to 2500 psig.

6. The process of claim 1 wherein the polyol has the formula:

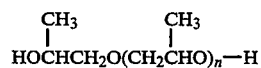

where n=about 33.1 or 84.7 and the catalyst consists essentially of nickel and copper deposited on a support in a ratio between 10:1 and 1:3 and amination is performed at a temperature of 180° C. to 220° C. and a pressure of 1500 psig to 2500 psig.

7. In a process for the amination of alcohols to form primary amines which comprises reacting a polyoxyalkylene alcohol or polyol having a molecular weight of from 230 to 5000 with ammonia in the presence of hydrogen the improvement comprising accomplishing the reaction at a temperature of 100° C. to 300° C. and a pressure of 300 psi to 5000 psi in the presence of a catalyst composition consisting essentially of:

θ-alumina on which there has been deposited nickel and copper in the form of nitrate hydrates at a temperature of 60° C. to 80° C., drying the catalyst overnight at 110° C. to 130° C., repeating said depositing and drying steps, and calcining said catalyst for 3–5 hours at 380°–420° C., forming supported metal oxides, wherein the total active metal loading is 10–40 wt % of the catalyst as metal and at least 50 wt % of the total catalyst is θ-alumina, resulting in a metal loading of 15–30 wt % nickel, 3–20 wt % copper and, optionally, 0.5–1 wt % molybdenum.

8. The process of claim 7 wherein the ratio of polyol to ammonia reactants is from 1:3 to 3:1 wt/wt and the amount of hydrogen reactant is 0.5 to 3.0 ScF/lb of polyol.

9. The process of claim 7 wherein the polyol has the formula:

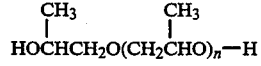

where n=about 33.1 or 84.7 and the catalyst consists essentially of nickel and copper deposited on a support in a ratio between 10:1 and 1:3 and amination is performed at a temperature of 180° C. to 220° C. and a pressure of 1500 psig to 2500 psig.

10. The process of claim 7 wherein the θ-alumina support results from calcining a γ-alumina or pseudo-boehmite support for 2–4 hours at 900°–1100° C.

11. The process of claim 7 wherein the process takes place at a temperature of 180° C. to 240° C. and a pressure of 1500 psig to 2500 psig.

* * * * *